United States Patent [19]

Kraver

[11] Patent Number: 5,741,397
[45] Date of Patent: Apr. 21, 1998

[54] DENTAL WASTE SEPARATOR

[76] Inventor: Mark P. Kraver, 3001 Del Prado Blvd., Cape Coral, Fla. 33904

[21] Appl. No.: 584,343

[22] Filed: Jan. 11, 1996

[51] Int. Cl.[6] .................. C02F 1/08; B01D 1/24; A61L 2/04; A61L 2/24
[52] U.S. Cl. .............. 159/25.2; 159/28.4; 159/43.1; 159/47.3; 159/6.2; 422/309; 433/92
[58] Field of Search ................. 422/309, 105, 422/106, 119; 159/25.1, 25.2, 28.4, 43.1, 47.3, 42, 6.1, 44, 6.2, DIG. 16; 202/200, 238, 160, 164, 205; 203/2, 91; 433/92; 34/305, 413, 417, 520, 521, 85, 80, 81, 82, 179, 235, 236, 667

[56] References Cited

U.S. PATENT DOCUMENTS

| | | | |
|---|---|---|---|
| 4,073,677 | 2/1978 | Noda et al. | 159/13.2 X |
| 5,205,743 | 4/1993 | Ludvigsson et al. | 433/92 |
| 5,418,982 | 5/1995 | Kishi | 4/111.1 |
| 5,445,714 | 8/1995 | Myers | 159/901 X |
| 5,564,133 | 10/1996 | Kishi | 422/309 X |

Primary Examiner—Robert J. Warden
Assistant Examiner—E. Leigh Dawson
Attorney, Agent, or Firm—William E. Noonan

[57] ABSTRACT

An apparatus is provided for processing combined liquid and solid dental waste from a patient's mouth such that the solid waste is separated from the liquid waste. The solid and liquid dental waste are removed from the patient's mouth and transmitted to a separation chamber. The liquid waste is substantially eliminated from the separation chamber to leave a solid waste residue therein. The solid waste residue is then collected from the separation chamber.

20 Claims, 4 Drawing Sheets

DENTAL WASTE SEPARATOR

FIELD OF THE INVENTION

This invention relates to a dental waste separator and, more particularly, to an apparatus for separating solid dental waste from dental waste water after such waste has been removed from a patient's mouth by a standard dental suction.

BACKGROUND OF THE INVENTION

Dental waste normally comprises a variety of solid and liquid materials. Solids may include tooth particles as well as metallic and ceramic pieces that compose amalgams, fillings and crowns. Gold, silver, palladium and mercury are typical of the metals that are often present in dental waste. These solid materials may be accompanied by a variety of liquid waste substances, including saliva, blood and rinse water. Saliva and blood each comprise solids and water.

Traditionally, both liquid and solid dental waste has been disposed of simply by flushing the combined waste into either the municipal sewer system or the dentist's septic system. However, this technique is rapidly becoming unacceptable. Increasingly strict environmental regulations now often prohibit the disposal of potentially toxic materials such as mercury into the environment. Additionally, it is obviously beneficial to retrieve and recycle the valuable metals, such as gold, silver and palladium, that are often found in dental waste.

Currently, few devices are available for effectively separating solid dental waste from liquid waste materials. Fairly simple traps and filters are known; but these devices do not satisfactorily extract minute solid particulates. More complicated separators, as well as chemical and electrical separation approaches have also been proposed. However, these techniques are usually quite expensive and the equipment requires constant maintenance, repair and replacement. An additional problem with available separator mechanisms is that they do not adequately sterilize the extracted solid particles. Dental waste may be contaminated with a number of types of germs and viruses. Blood and saliva may even carry the AIDS virus. It is critical that dental waste be separated in such a way that the extracted solids are sterilized from such contamination.

SUMMARY OF INVENTION

It is therefore an object of this invention to provide an improved apparatus for effectively separating solid dental waste from dental waste water.

It is a further object of this invention to provide a dental waste separator that safely sterilizes the solid dental waste removed from a patient's mouth.

It is a further object of this invention to provide a dental waste separator that effectively extracts potentially hazardous substances such as mercury from dental waste so that the municipal sewer system, ground water or the dentist's septic system are not contaminated with these hazardous waste products.

It is a further object of this invention to provide a dental waste separator that permits dental waste to be disposed of in conformance with environmental, safety and health laws and regulations.

It is a further object of this invention to provide a dental waste separator that effectively extracts and recovers potentially valuable metals from a patient's dental waste so that such materials may be reprocessed or recycled.

It is a further object of this invention to provide a dental waste separator that utilizes a relatively simple and inexpensive, yet highly effective construction.

This invention results from a realization that solid materials may be effectively extracted from dental waste and, at the same time, safely sterilized by heating the dental waste in an autoclave or a similar pressurized separation chamber. The invention features an apparatus for processing combined liquid and solid dental waste from a patient's mouth such that the solid waste is separated from the liquid waste. The apparatus includes means for removing the combined solid and liquid dental waste from the patient's mouth. There is a separation chamber and means for transmitting the combined solid and liquid dental waste from the means for removing to the separation chamber. There are means for substantially eliminating the liquid waste from the separation chamber to leave a solid waste residue therein. Means are provided for collecting the solid waste residue from the separation chamber.

In a preferred embodiment, the means for removing includes a suction device. This may be a dry suction device commonly found in a dental office. The separation chamber may include a sealed container and, more particularly, may comprise an autoclave.

The means for transmitting preferably includes a storage container for receiving and temporarily storing the combined solid and liquid waste. The means for transmitting may also include valve means that interconnect the storage container and the separation chamber. Control means may be employed to operate the valve means automatically. The valve means are alternately opened to introduce the combined solid and liquid waste into the separation chamber and closed to retain the pressure and heat in the separation chamber. Means may be provided for automatically stopping the means for removing when waste in the storage container reaches a predetermined level. Means may also be provided for indicating that the waste in the storage container is at a predetermined level.

The means for substantially eliminating waste liquids may include means for raising the temperature and pressure inside the separation chamber to a level that causes the liquid dental waste to boil and evaporate. The chamber may include an outlet through which the evaporated liquid is vented. The means for raising temperature and pressure may include heating coils that are mounted adjacent to and/or under the separation chamber.

The means for transmitting may further include a secondary container (preferably a cylinder) disposed between storage container and the separation container. A first valve may interconnect the storage container and the cylinder. The first valve is alternately opened to introduce combined liquid and solid waste into the cylinder and closed to retain waste in the storage container. The second valve may interconnect the cylinder and the separation chamber. The second valve is alternately opened to introduce liquid and solid waste from the cylinder into the separation chamber and closed to temporarily retain subsequently generated waste in the cylinder. Means may be provided for sensing that a predetermined volume of combined liquid and solid waste is collected in the storage container. Control means, responsive to the means for sensing, may automatically open the valve means when the predetermined level is sensed to deliver waste to the separation chamber. The device may further employ means for sensing and indicating that the predetermined level of waste has been collected in the container but that the valve means have not automatically opened. The storage container may include a holding tank portion and an overflow tank portion. The first valve is preferably interconnected between the holding tank portion and the cylinder. A third valve is preferably interconnected between the overflow tank portion and the cylinder. The third valve is alternately opened to transmit waste from the overflow tank portion to the cylinder and closed to restrict water in the overflow from entering the cylinder.

The means for venting may further include filter means for removing toxic vapors from the evaporated liquid. Control means may be utilized to automatically operate the valve means, the means for substantially eliminating and the means for collecting in a predetermined manner to process the combined solid and liquid dental waste such that the solid waste is separated from the liquid waste

BRIEF DESCRIPTION OF THE DRAWINGS

Other objects, features and advantages will occur from the following description of preferred embodiments and the accompanying drawings, in which.

DETAILED DESCRIPTION OF PREFERRED EMBODIMENTS

Figure 1:
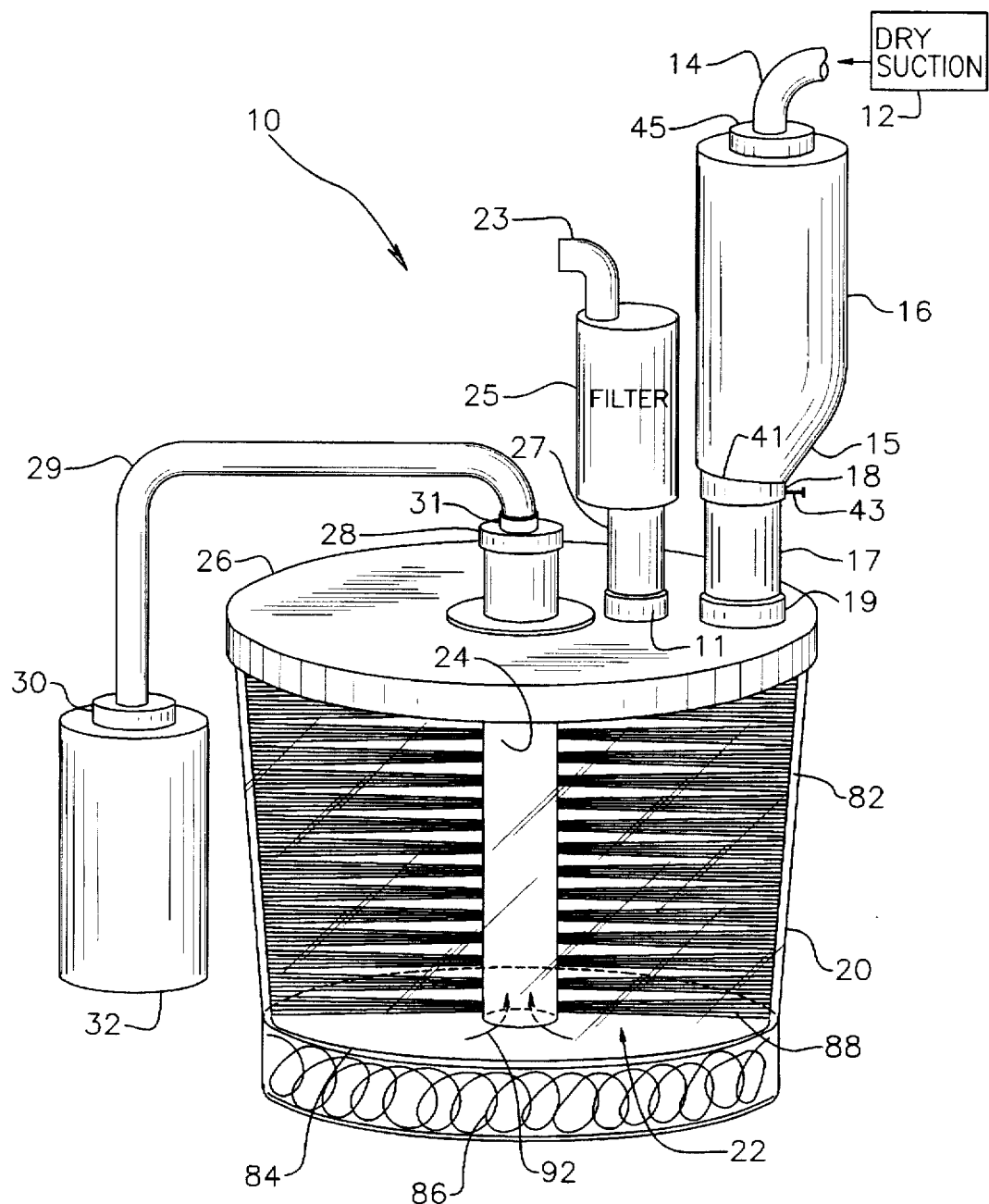
FIG. 1 is a perspective, partly cut away and partly schematic view of a preferred dental waste separator according to this invention.

There is shown in FIG. 1 a dental waste separator 10. The separator includes a conventional dry suction device 12, which removes combined liquid and solid dental waste from a patient's mouth. Device 12 may comprise any of the various known suction devices that are presently used in most dental practices. These devices typically remove the dental waste from a patient with or without adding additional water to the waste. A suction hose 14 communicably interconnects suction device 12 with a storage container 16, described more fully below. The lower discharge end 15 of container 16 is communicably joined through a valve assembly 18 to the upper end of a secondary container comprising a graduated cylinder 17.

The lower end of a cylinder 17 is communicably interconnected by a second, graduated cylinder valve assembly 19 to a separation chamber 20. The separation chamber comprises a sealed container that includes a generally frustoconical side wall 82 and a lid 26 sealably attached to side wall 82. A floor portion 84 is unitarily attached to the lower end of side wall 82. A plurality of conventional heating coils 86 are disposed beneath floor 84. In alternative embodiments, the heating coils may be formed through the side wall 82. Separation chamber 20 may constitute or closely resemble an autoclave or pressure cooker. High temperatures and pressures are generated within the interior of chamber 20 so that the function and benefits of this invention are accomplished.

The separation container accommodates a rotary brush mechanism 22. The brush mechanism includes an axial shaft, which comprises a vacuum hose 24. This hose extends through a sealed lid 26 of container 20 and through a standard DC motor 28 that drives brush mechanism 22. In alternative embodiments, the brushes may be driven as in FIG. 5, described more fully below. The hose also comprises the shaft of motor 28. Brush assembly 22 includes multiple rows of bristles 88 that are attached to and extend radially outwardly from the exterior surface of hose 24. The bristles are sufficiently long to engage the interior surface of frustoconical side wall 82. When motor 28 operates, hose 24 is rotated by the motor such that bristles 88 sweep the inside surface of side wall 82. In this manner, hose 24 serves as the rotatable shaft or axle of brush assembly 22.

An evaporation valve 11 is formed in lid 26 of chamber 20. Valve 11, which may comprise various known types of automatically controlled valves, is opened, as described below, to release evaporated water and accompany mercury vapor from chamber 20 through an outlet 27. This outlet directs the evaporated material to an activated filter 25 commonly used in industrial applications. A discharge vent 23 is connected to filter 25.

A collection hose 29 is communicably joined to hose 24 through a standard rotatable bearing seal 31. Hose 29 is itself attached to a collection vacuum 30. A solid waste storage receptacle 32 is operably connected to vacuum 30. The vacuum collects extracted solid dental waste from chamber 20 and deposits it in receptacle 32, likewise in the manner described below. Vacuum 30 and solid waste storage receptacle 32 typically comprise a standard dry industrial vacuum collection mechanism such as a Shop Vac (TM) device or similar apparatus. The version used for separator 10 should be relatively compact so that it conveniently fits in available space in a dental office. Normally, vacuum 30 and waste storage receptacle 32 are placed in a hidden unobtrusive location such as a closet, storage room, vanity, etc.

Figure 2:
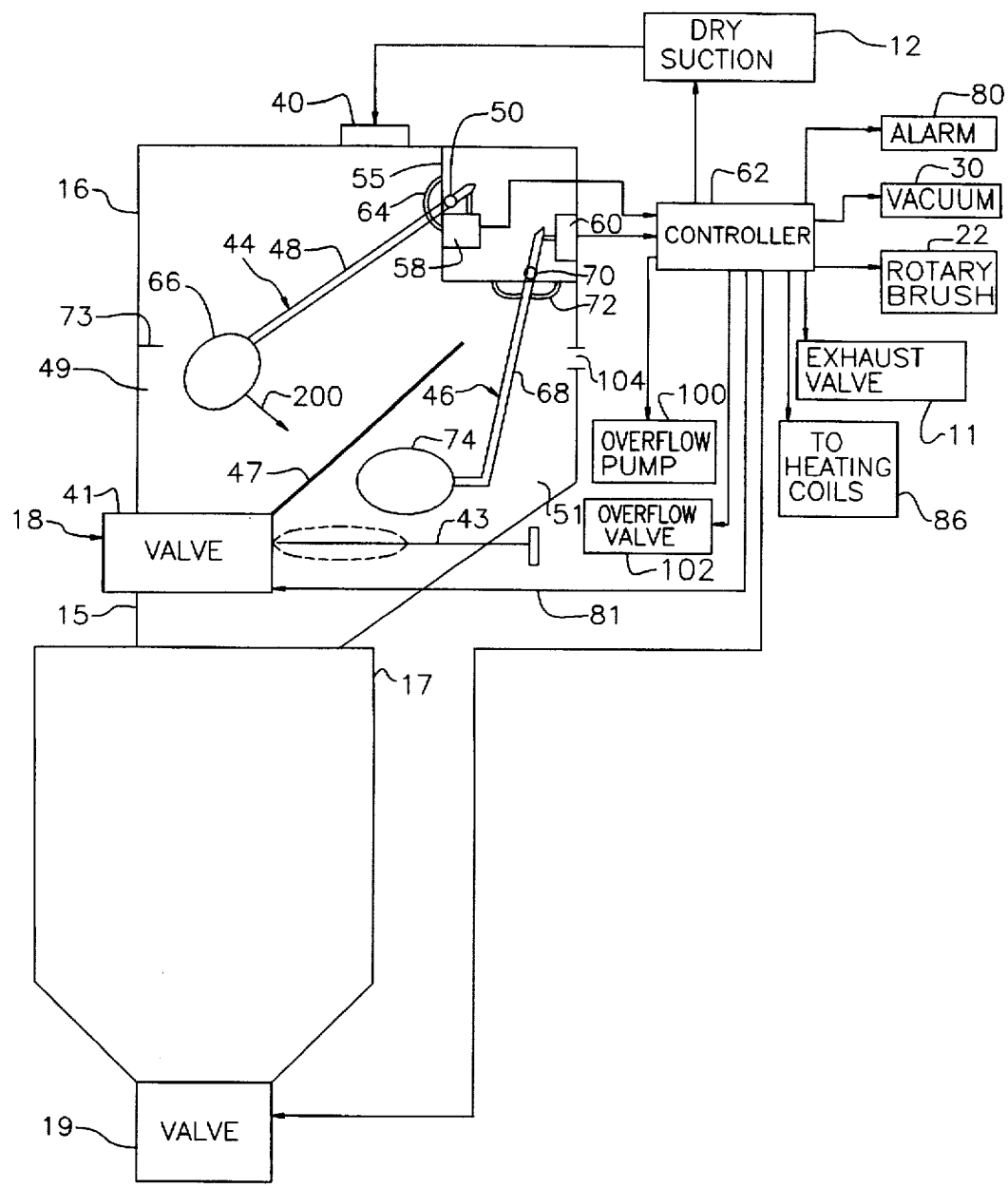
FIG. 2 is a schematic view of a preferred means for removing, means for transmitting and controller used in the separator.

A preferred suction storage container 16 is illustrated in FIG. 2. Container 16 includes an inlet 40 formed at its upper end. Lower discharge end 15 carries valve assembly 18 comprising a standard automatic, relay controlled holding tank valve 41 and a conventional manual valve 43 adjacent valve 41. These valves are operated in the manner described below. Suction hose 14 is operably connected in a known fashion to inlet 40 by a fitting 45, shown in FIG. 1.

The interior of container 16 is divided by a wall 47 that extends generally diagonally from valve 41 through container 16. The space generally above and to the left of wall 47 defines a holding tank 49. The space generally below and to the right of wall 47 defines an alarm overflow tank 51. A relay housing 55 is mounted within container 16 above wall 47. In FIG. 2, housing 55 is shown in the upper right hand corner of container 16, although in alternative embodiments, this housing may be placed at other locations within the container. A pair of relay switches 58 and 60 are mounted in an appropriate manner within housing 55. It is possible that waterproof relay switches may be utilized and mounted directly to the inside wall of container 16. In such cases, housing 55 may be eliminated entirely. The relay switches are electrically interconnected to a controller 62, which may comprise various known types of microprocessors or other types of controller devices. The controller may be programmed in a conventional manner to receive inputs from and direct operation of the various components described herein. The operation of the controller is described more fully below.

A pair of float assemblies 44 and 46 are operably mounted within container 16. Float assembly 44 includes a shaft 48 that is connected by a pivot 50 to the inside wall of container 16 within housing 55. Shaft 48 extends through a flexible grommet 64 that is formed in the side wall of housing 55. The distal end of shaft 48 is located in holding tank 49 and carries a float element 66. The opposite inner end of shaft 48 operably engages relay switch 58.

Float assembly 46 includes a bent shaft 68 that is similarly mounted by a pivot 70 to the inside wall of container 16 within housing 55. Shaft 68 extends outwardly through housing 55 and, more particularly, through a flexible grommet 72. The lower bent portion of shaft 46 is disposed within alarm overflow tank 51. The distal end of the shaft carries a second float element 74. The opposite inner end of shaft 68 operably engages relay switch 60. Grommets 64 and 72 permit the float assemblies to pivot within container 16 and at the same time seal housing 55 so that liquid is not allowed to enter the housing. Float assemblies 44 and 46 resemble the float assemblies normally found in toilet tanks. Other known float structures may also be employed. The relay switches may comprise toggle switches or other cam activated switching mechanisms.

The float shafts 48 and 68 of float assemblies 44 and 46 operate relay switches 58 and 60, respectively. More specifically, as each float assembly pivots, its shaft engages and disengages its corresponding relay switch so that the switch is alternated in a known manner between first and second, (i.e. "off" and "on" states). Operation of the float assemblies and corresponding relay switches is described more fully below.

Automatic valve 41 remains closed when the volume of waste in holding tank 49 of container 16 is below a predetermined level (corresponding to the volume of cylinder 17) and which opens when the waste volume exceeds that level. Controller 62 is connected to valve 41 by a line 81. Valve 41 is opened and closed by the operation of float assembly 44 and switch assembly 58. When the volume of dental waste in tank 49 is below a predetermined level 73, the weight of float member 66 causes float bar 52 to pivot downwardly, as indicated by arrow 200 (or to remain in this position). As a result, the opposite end of the float bar is disengaged from switch 58 or otherwise maintains switch 58 in its first ("off") state. Controller 62 senses that switch 58 is off and holds valve 18 closed. When the level of waste in container 16 rises to predetermined level 73, float element 66 rises and causes float bar 48 to engage switch 58 and alternate that switch from its first to its second ("on") state. An appropriate signal is transmitted to controller 62, which directs valve 41 to open for a set time. As a result, a predetermined volume of dental waste is discharged from container 16 through valve 41.

It should be noted that a wide variety of alternative valve mechanisms may be utilized. For example, switch 58 and controller X may be eliminated and float arm 48 may be connected to valve 41 by a chain, strap or other connector. The valve itself may comprise a standard toilet flap valve. In such cases, when the waste in tank 49 rises to level 73, float arm 48 pivots and pulls valve 41 open to release the waste contents from container 16 through valve 41. Various other techniques may be used for periodically opening valve 41. For example, the separator may be automated by employing a conventional timing mechanism that opens valve 41 at predetermined times and for predetermined durations regardless of the amount of waste present in tank 49.

Float assembly 46 and associated relay switch 60 are employed as a safety feature to prevent container 16 from overflowing and/or backing up if valve 41 fails to open properly. In such cases, dental waste in tank 49 overflows the upper end of wall 47 and collects in alarm overflow tank 51. Eventually, this overflow waste causes float member 74 to rise. As a result, arm 68 pivots about pivot 70 and operably engages switch 60, which is alternated from an "off" state to an "on" state. This sends an input signal to controller 62 which, in turn, is programmed to send an output signal to dry suction 12 and/or an alarm 80. When the output signal is received by dry suction apparatus 12, the suction apparatus is deactivated so that no additional dental waste is sent to container 16. An output signal may also activate optional alarm 80 so that the dental staff receives a visual and/or audible warning that the level of waste in container 16 is approaching capacity. In either event, the user should check and reduce the waste level in tank 51. The handle of manual valve 43 is turned to open the valve (as shown in phantom) and discharge the waste from tank 51. Automatic deactivation of the dry suction and/or activation of alarm 80 indicates that there is a problem with at least one of valve 41, switch assembly 58 and float assembly 44. The user may then address and remedy that problem by appropriate repair or replacement of the defective part(s).

Optional controller 62 receives inputs and provides outputs that are appropriate for automatically controlling the operation of apparatus 10. As previously described, controller 62 receives input signals from relay switches 58 and 60. The controller may also receive inputs from an overflow pump 100 and an overflow valve 102, the operation of which are described more fully below in connection with FIG. 3. As previously explained, controller 62 directs valve 41 to automatically open when relay switch 58 is activated. The controller is likewise interconnected with valve 19, located at the lower end of graduated cylinder 17. When a predetermined amount of liquid waste is emptied into graduated cylinder 17, the controller is programmed to automatically close valve 41 and open valve 19. As a result, a predetermined amount of liquid waste in cylinder 17 is introduced into separation chamber 20, FIG. 1. This is specifically accomplished by programming the controller so that valve 41 is directed to open for a predetermined time (i.e. 2 seconds). This time will allow a pre-measured amount of waste to collect in the graduated cylinder. The precise amount and the time required for that amount should be calculated so that waste is efficiently treated in chamber 20 and energy, is not wasted. The precise specifications are not a limitation of this invention.

Controller 62 provides outputs to and automatically controls the operation of a number of the components of apparatus 10. In particular, as shown in FIG. 2, the controller provides outputs to dry suction 12, alarm 80 (described above), rotary brush motor 28, exhaust valve 11, heating coils 86, vacuum 30, overflow pump 100 and valve 102. Various types of microprocessors or other controllers may be utilized and the controller is operably interconnected to the various components of the system through solenoids or other conventional means.

Figure 3:
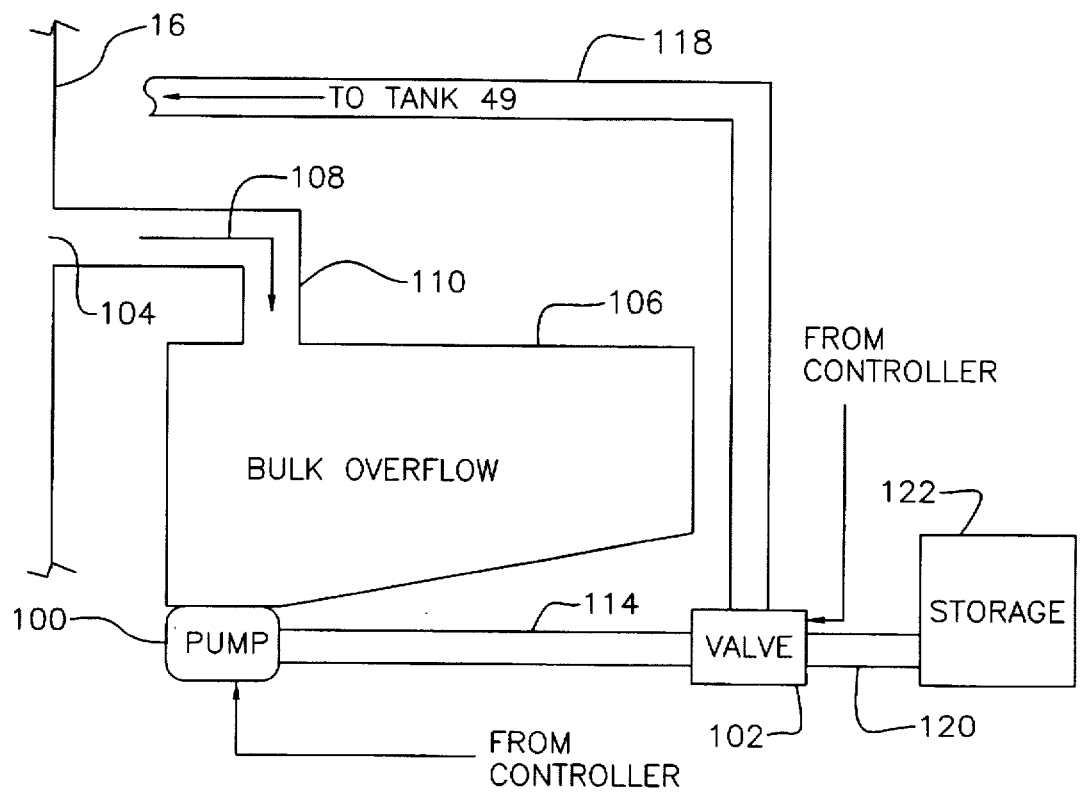
FIG. 3 is a schematic view of an optional bulk overflow tank that may be used for the holding container.

Alarm overflow tank 51 may be equipped with an overflow port 104, particularly when the apparatus is used in busy dental practices wherein repairs often cannot be performed in a timely manner. As illustrated in FIG. 3, port 104 is communicably connected to a bulk overflow tank 106. This may be located at a remote, convenient location outside the office. If apparatus 10 is not provided with a manual valve 43 (as illustrated in FIG. 2) or if the separation chamber is temporarily inoperable, a bulk overflow tank 106 is beneficial for storing the excess overflow waste generated in the dental practice. Tank 106 should be located somewhat below tank 51 to take advantage of gravity. Alternatively, if tank 51 is not allowed to use gravity to fill tank 106, a pump, not shown, should be employed to remove the excess overflow waste from tank 51 and lift it into the bulk overflow tank. As illustrated in FIG. 3, when the liquid waste level in tank 51 reaches the level of outlet 104, waste liquid is directed, as indicated by arrow 108 through a transmission conduit 110 into tank 106. After necessary repairs or maintenance have been performed, the liquid waste stored in tank 106 is returned to tank 49 of container 16. This is accomplished by overflow pump 100 that is communicably connected to a lower end of tank 106. Pump 100 is operated as required to direct liquid waste from tank 106 through a conduit 114. Overflow valve 102 directs this waste through a conduit 118 back into tank 49 of container 16. The liquid waste is then delivered back to graduated cylinder 17, FIG. 2, by opening valves 41 or 43.

Figure 4:
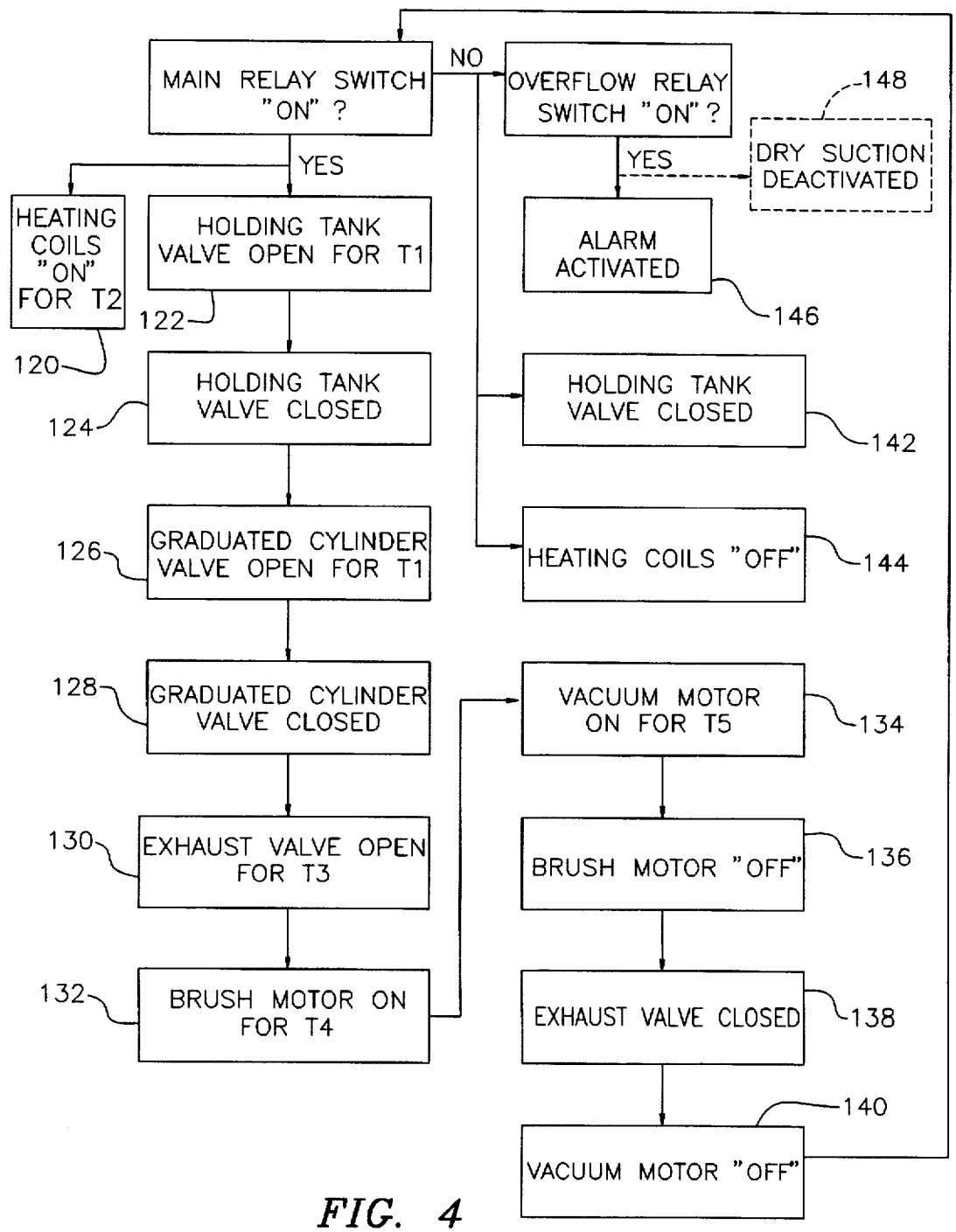
FIG. 4 is a block diagram of a preferred operating sequence for the controller used in this invention.

In cases where tank 106 is filled but apparatus 10 has not yet been fully repaired, the liquid overflow in tank 106 is removed from the tank, again by pump 100 and directed through conduit 114 to valve 102. This valve is adjusted to direct the waste through a conduit branch 120 to an additional storage tank 122. Both pump 100 and valve 102 may be operated either manually or by controller 62. Appropriate inputs from the controller are shown in FIG. 4. Pump 100 and valve 102 may comprise various types of known mechanisms.

Controller 62 may be programmed as shown in FIG. 4 so that separator 10 operates in the following manner. Initially, combined liquid and solid waste material, including blood, saliva, rinse water, tooth particles, ceramics and metals, are removed by dry suction 12 and deposited in suction storage container 16. When the dental waste first reaches predetermined level 73 within tank 49 of container 16, switch 58 is turned "on". As a result, controller 62 opens holding tank valve 41, step 120, and activates coils 86, step 122, thereby preheating chamber 20. A predetermined volume of waste is delivered to cylinder 17. After time T1, valve 41 is automatically closed, step 124, and graduated cylinder valve 19 is opened for a similar duration, step 126. The liquid waste is therefore delivered to chamber 20. Valve 19 is closed, step 128. This seals chamber 20. Heating coils 86 remain activated for a total duration of T2 (e.g. 15 minutes). Activating coils 86 raises the temperature within sealed chamber 20 to approximately 280° C. The pressure in the chamber is raised to approximately 20 p.s.i. This temperature and pressure are maintained for approximately to 5 to 10 minutes. As a result, the dental waste water evaporates into steam. At or near the end of the heating cycle, controller 62 opens exhaust valve 11, step 130, for a duration of T3 (e.g. 5 minutes). The evaporated water is discharged through evaporation outlet 27. Filter 25 removes harmful mercury vapors from the evaporated liquid. Drying may be accelerated by activating a blower, not shown, within chamber 20. The blower may be operated, as well, by controller 62. Drying may also be accelerated by operating vacuum 30 to increase air circulation in chamber 20.

When evaporation is substantially complete, all that remains within chamber 20 is sterilized solid dental waste, e.g. tooth particles and various metal, ceramic and synthetic residue from amalgams, crowns, etc. Some of this material coats the inside surface of frustoconical wall 82. Accordingly, motor 28 is operated to rotatably drive brush assembly 22. The motor may be started either at any time desired by the user or automatically by controller 62, step 132, for a time T4. As assembly 22 rotates, bristles 88 sweep the solid dental waste residue from the inside surface of wall 82 and that residue falls onto floor 84. Vacuum 30 is then activated, step 134, for a duration of T5. As a result, the solid residue is drawn in the direction of arrows 92, FIG. 1, from chamber 20 through hoses 24 and 29 and into solid waste storage receptacle 32. At regular or desired intervals, the collected solid waste from receptacle 32 is removed for reprocessing, recycling and/or disposal. Valuable and/or toxic metallic materials may be separated from other solid waste residue in a known manner.

Controller 62 completes its operation by deactivating brush motor 28, closing valve 11 and deactivating vacuum 30, steps 136, 138, 140. The entire process cycle is then repeated. If the controller senses that the waste in tank 49 has fallen below the predetermined volume 73 (e.g. switch 58 has been turned "off"), valve 41 is held closed, step 142, and previously active heating coils 86 are switched "off", step 144. Once dental waste is above predetermined volume 73 and the coils are activated, they will remain on for a full T2 (15 minutes) even if this duration continues after switch 58 is deactivated.

In some cases, switch 58 may malfunction and liquid may overflow into tank 51, even with switch 58 in the "off" condition. This causes float assembly 46 to activate switch 60. As a result, alarm 80 is activated, step 146. The dry suction 12 and heating coils 86 may also be disabled, step 148.

Figure 5:
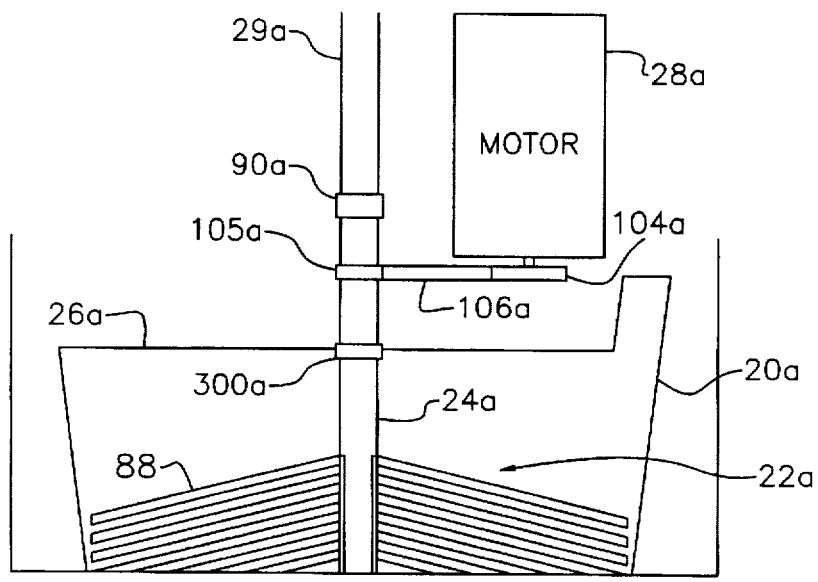
FIG. 5 is a schematic view of the upper end of the separation chamber and an alternative motor assembly for driving the rotary brush within the separation chamber.

An alternative motor assembly 28a is illustrated in FIG. 5. Therein, separation chamber 20a again accommodates a brush assembly 22a. The rotatable shaft 24a of the brush assembly comprises a vacuum hose, as previously described. Hose 24a extends through a conventional bearing and seal housing 300a formed in lid 26a. The upper end of rotatable hose 24a is rotatably and communicably joined to a stationary hose 29a by a second bearing and seal housing 90a. Motor 28a may or may not be mounted directly to lid 26a, and may be secured to adjacent structure, not shown. The drive shaft of motor 28a carries a conventional pulley assembly 104a. That pulley is operably connected by a drive belt 106a to a second pulley 105a. The latter is mounted to the portion of rotating hose 24a that extends outside of separation chamber 20a. In operation, motor 28a drives pulley 104a to axially rotate hose 24a. This rotates brush assembly 22a in the manner previously described. While hose 24a rotates, hose 29a remains stationary. Otherwise, this embodiment operates identically to the previously described version.

The components of this invention are typically constructed of various durable and high strength materials such as those that are commonly used in the dental and medical industries. The separation chamber should employ a construction that is capable of withstanding the heat and pressure conditions required to perform the liquid waste evaporation, sterilization and solid waste extraction described herein. The particular components used for the dry suction device, suction container, valves, vacuum and solid waste storage container comprising various conventional off-the-shelf components that will be known to those skilled in the art. The controller may be programmed in various sequences and in certain embodiments may be eliminated entirely.

Accordingly, the present invention permits various solid dental waste materials to be safely and effectively collected so that they may be reprocessed or discarded in an effective manner. The separator meets all present environmental standards by eliminating the disposal of mercury and other toxic metals into the public sewer or septic system. Additionally, valuable metals can be collected, redeemed and reprocessed using this apparatus. This invention effectively sterilizes the extracted solid waste elements and eliminates potentially dangerous viruses and germs often present in liquid dental waste. The high temperatures and pressures utilized by the separator virtually eliminate any possibility of such contamination remaining on the extracted solid waste material. The separator also employs a very efficient and low cost construction that should be affordable to most dental offices.

Although specific features of the invention are shown in some drawings and not others, this is for convenience only, as each feature may be combined with any or all of the other features in accordance with the invention. Other embodiments will occur to those skilled in the art and are within the following claims.

What is claimed is:

1. An apparatus for processing combined liquid and solid dental waste from a patient's mouth such that the solid waste is separated from the liquid waste and sterilized, said apparatus comprising:

suction means for removing the combined solid and liquid dental waste from the patient's mouth;

a single, stationary separation chamber;

means for transmitting the combined solid and liquid dental waste from said suction means to said separation chamber;

means for raising the temperature and pressure inside said separation chamber to a level that evaporates the liquid dental waste and sterilizes the solid dental waste;

means for venting the evaporated liquid from said chamber;

means for extracting mercury vapors from the evaporated liquid; and means for collecting the sterilized solid waste residue from said separation chamber.

2. The apparatus of claim 1 in which said means for removing includes a suction device.

3. The apparatus of claim 1 in which said means for collecting include vacuum means communicably connected to the interior of said separation chamber for drawing the solid waste residue from said separation chamber.

4. The apparatus of claim 3 which said means for collecting further includes a receptacle attached to said vacuum means for receiving and storing solid waste pulled out of said separation chamber.

5. The apparatus of claim 1 in which said means for transmitting include a storage container for receiving and storing the combined solid and liquid waste.

6. The apparatus of claim 5 in which said means for transmitting include valve means interconnected between said storage container and said separation chamber for selectively introducing combined solid and liquid waste into said separation chamber.

7. The apparatus of claim 6 further including control means for automatically operating said valve means, said means for raising and said means for collecting in a predetermined manner to process combined solid and liquid dental waste such that the solid waste is separated from the liquid waste.

8. The apparatus of claim 6 further including means for sensing that a predetermined volume of combined liquid and solid waste is collected in said storage container and control means, responsive to said means for sensing for automatically opening said valve means when said predetermined volume is sensed to deliver said waste to said separation chamber.

9. The apparatus of claim 8 further including means for sensing and indicating that said predetermined level of waste has been collected in said container and that said valve means have not automatically opened.

10. The apparatus of claim 5 in which said means for transmitting further includes a secondary container disposed between said storage container and said separation chamber, first valve means interconnected between said storage container and said secondary container for selectively introducing combined liquid and solid waste into said secondary container and second valve means interconnected between said secondary container and said separation chamber for selectively introducing said liquid and solid waste from said secondary chamber into said separation chamber.

11. The apparatus of claim 10 in which said storage container includes means for dividing said storage container into a holding tank portion and an alarm overflow tank portion, said first valve means being interconnected between said holding tank portion and said secondary container, and further including third valve means, interconnected between said alarm overflow tank portion and said secondary container, for selectively transmitting waste from said overflow tank portion to said secondary container.

12. The apparatus of claim 1 in which said means for collecting includes a rotary brush mounted within said separation chamber and engaging an interior side wall of said chamber and means for rotating said brush to sweep said interior side wall of said chamber such that solid waste residue is dislodged therefrom.

13. The apparatus of claim 12 in which said means for collecting include vacuum means communicably connected to the interior of said separation chamber for drawing the solid waste residue from said separation chamber, said vacuum means including a vacuum channel, formed axially through said brush and extending through and exteriorly of said separation chamber, and a vacuum generating device operably attached to said vacuum channel outside of said chamber for pulling solid waste residue out of said separation chamber through said vacuum channel.

14. The apparatus of claim 13 in which said means for rotating includes a rotary motor.

15. The apparatus of claim 1 further including exhaust valve means for selectively introducing evaporated liquid into said vent means.

16. The apparatus of claim 1 in which said separator chamber includes an autoclave.

17. A method for processing combined liquid and solid dental waste from a patient's mouth such that the solid waste is separated from the liquid waste and sterilized, said method comprising the steps of:

sucking combined solid and liquid dental waste from the patient's mouth;

transmitting the combined solid and liquid dental waste to a single, stationary separation chamber;

raising the temperature and pressure inside the separation chamber to levels that evaporate the liquid dental waste and sterilize the solid waste;

venting evaporated water from said chamber;

extracting mercury vapor from evaporated liquid; and collecting the sterilized solid waste residue from the separation chamber.

18. The method of claim 17 in which the temperature in the separation chamber is raised to approximately 280 degrees centigrade and the pressure within the chamber is raised to approximately 20 p.s.i.

19. The method of claim 18 in which the elevated temperature and pressure are maintained for at least 5 minutes and not greater than 10 minutes.

20. A method for processing combined liquid and solid dental waste from a patient's mouth such that the solid waste is separated from the liquid waste and sterilized, said method comprising the steps of:

sucking combined solid and liquid dental waste from the patient's mouth;

transmitting the combined solid and liquid dental waste to a single, stationary separation chamber;

raising the temperature and pressure inside the separation chamber to levels that evaporate the liquid dental waste and sterilize the solid waste;

venting evaporated water from said chamber; and collecting the sterilized solid waste residue from the separation chamber.

* * * * *